(12) United States Patent
Chomczynski

(10) Patent No.: US 7,794,932 B2
(45) Date of Patent: Sep. 14, 2010

(54) REAGENTS AND METHODS FOR ISOLATION OF PURIFIED RNA

(76) Inventor: Piotr Chomczynski, 14 Elmhurst Pl., Cincinnati, OH (US) 45208

( * ) Notice: Subject to any disclaimer, the term of this patent is extended or adjusted under 35 U.S.C. 154(b) by 293 days.

(21) Appl. No.: 10/826,113

(22) Filed: Apr. 16, 2004

(65) Prior Publication Data

US 2005/0233333 A1 Oct. 20, 2005

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | | |
|---|---|---|---|---|
| 3,163,638 A | 12/1964 | Miwa et al. | .............. | 260/211.5 |
| 4,843,155 A | 6/1989 | Chomczynski | ............... | 536/27 |
| 5,346,994 A * | 9/1994 | Chomczynski | .............. | 530/419 |
| 5,945,515 A | 8/1999 | Chomczynski | .............. | 530/412 |
| 5,973,137 A | 10/1999 | Heath | ........................ | 536/25.4 |

FOREIGN PATENT DOCUMENTS

| | | |
|---|---|---|
| WO | 0 611 157 | 8/1994 |
| WO | WO 95/28409 | 10/1995 |
| WO | WO 98/04730 | 2/1998 |
| WO | WO 01/46402 | 6/2001 |
| WO | WO 01/96351 | 12/2001 |

OTHER PUBLICATIONS

Chen et al (Chinese patent 1,220,995, translation).*
Focus (1998) 20(2):36.*
Chen et al. (Chinese patent 1,220,995, translation provided).*
Focus (1998) 20(2):36.*
American Chemical Society, *Most Cited Journal Articles 2002*, CAS Science Spotlight, Chemistry & Related Science, Journal Articles, 2002, http:/www.cas.org/spotlight/jcite02/jcite02.html.
Bonham, M.J. et al., *Improved Purification and Yields of RNA by RNeasy*, BioTechniques 21:57-60, (1996).
Chattopadhyay, N. et al, *Inexpensive SDS-Phenol Method for RNA Extraction from Tissues*, BioTechniques, 15:24-25 (1993).
Chomczynski, P. et al, *Modification of the TRI Reagent Procedure for Isolation of RNA from Polysaccharide- and Proteoglycan-Rich Sources*, Short Technical Reports, BioTechniques, 19:942-945 (1995).
Chomczynski, Piotr, *A Reagent for the Single-Step Simultaneous Isolation of RNA, DNA and Proteins from Cell and Tissue Samples*, BioTechniques, 15:532-535 (1993).
Chomczynski, P. et al, *Single-Step Method of RNA Isolation by Acid Guanidinium Thiocyanate-Phenol-Chloroform Extraction*, Anal. Biochem. 162:156-159 (1987).
Girotti, M. et al, *Gene Expression Profiling of Rat Uterus at Different Stages of Parturition*, Endocrinology 144:2254-2265.
Guan, H.P. et al, *A futile metabolic cycle activated in adipocytes by antidiabetic agents*, Nature Med. 8:1122-1128 (2003).

Kedzierski, W. et al, *A Novel Non-Enzymatic Procedure for Removing DNA Template from RNA Transcription Mixtures*, BioTechniques 10:210-214 (1991).
Kingston, Robert E., *Preparation and Analysis of RNA*, Current Protocols in Molecular Biology, John Wiley & Sons, Inc., New York, vol. 1, 2002, Chapter 4, 4.0.1.-4.3.4.
Liu, Z. et al, *An Improved Rapid Method of Isolating RNA from Cultured Cells by SDS-Acid Phenol/Chloroform Extraction*, BioTechniques 16:56-57 (1994).
Mathy, N. L. et al, *Removal of RT-PCR Inhibitors from RNA Extracts of Tissues*, BioTechniques 21:770-774 (1996).
Molecular Research Center, *Tri Reagent—RNA, DNA, Protein Isolation Reagent*, Manufacturer's Protocol, pp. 1-6 (2003).
Monstein, H.J. et al., *RNA Extraction from Gastrointestinal Tract and Pancreas by a Modified Chomczynskl and Sacchi Method*, BioTechniques 19:340-343 (1995).
Mutimer, H. et al, *Pitfalls of Processed Pseudogenes in RT-PCR*, BioTechniques 24:585-587 (1998).
Puissant, C. et al, *An Improvement of the Single-Step Method of RNA Isolation by Acid Guanidinium Thiocyanate-Phenol-Chloroform Extraction*, BioTechniques 8:148-149 (1990).
ScienceWatch, *Twenty Years of Citation Superstars*, ScienceWatch, Sep.-Oct. 2003, http:/www.sciencewatch.com/sent-oct2003/sw_sept-oct2003_page2.html.
Siebert, Paul D. et al, *Modified acid guanidinium thiocyanate-phenol-chloroform RNA extraction method which greatly reduces DNA contamination*, Nucleic Acid Res. 21:2019-2020 (1993).
Simms, *RNA Isolation Reagent and Methods*, U.S. Patent Application Publication No. 20030204077, Oct. 30, 2003 (U.S. Appl. No. 10/442,946).
Suzuki, Y. et al, *Extraction of Total RNA from Leaves of Eucalyptus and Other Woody and Herbaceous Plants using Sodium Isoascorbate*, BioTechniques 34:988-993 (2003).
Monstein, et al., *RNA Extraction from Gastroinestinal Tract and Pancreas by a Modified Chomczynski and Sacchi Method*, BioTechniques (1995), vol. 19, pp. 340-344.
PCT, *International Search Report*, PCT/US2005/012814, mailed Jul. 29, 2005, 5 pages.
Wallace, *Large- and Small-Scale Phenol Extractions*, Methods in Enzymology (1987), vol. 152, pp. 33-48.

(Continued)

*Primary Examiner*—Christopher M. Babic
(74) *Attorney, Agent, or Firm*—Wood, Herron & Evans, LLP

(57) ABSTRACT

Compositions and methods to isolate intact RNA that is substantially free of DNA, termed purified RNA. RNA from any source (e.g., human, other animals, plants, viruses, etc.) may be isolated. In one embodiment, the sample is treated with phenol at a pH less than 4.0 and purified RNA is recovered from the aqueous phase. In another embodiment, RNA is precipitated from an acidified sample containing a low volume of an organic solvent. Other embodiments are disclosed. The same inventive composition may be used for several embodiments with pH adjustment. Purified RNA obtained by the inventive method may be used in assays where DNA contamination is undesirable, such as the polymerase chain reaction.

24 Claims, No Drawings

OTHER PUBLICATIONS

Chinese Patent Office, First Office Action, Chinese PCT National Phase Patent Application No. 200580017853.5, 3 pages.
Chinese Patent Office, English Translation of First Office Action, Chinese PCT National Phase Patent Application No. 200580017853.5, 2 pages.
Dominic, et al., "Cyanobacteria From Extreme Acidic Environments", http://www.ias.ac.in/currsci/oct25/articles14.htm, uploaded to world wide web on Aug. 26, 2004, 5 pages.
United States Patent and Trademark Office, Official Action directed to U.S. Appl. No. 11/931,723, mailed Jul. 8, 2009, 24 pages.

* cited by examiner

US 7,794,932 B2

REAGENTS AND METHODS FOR ISOLATION OF PURIFIED RNA

FIELD OF THE INVENTION

The invention is directed to compositions and methods that enhance isolation of purified RNA from biological samples.

BACKGROUND

Isolation of pure, intact RNA is a critical step for analysis of gene expression in molecular biology, clinical, and biotechnology applications. Methods of RNA isolation have been developed in an attempt to achieve this goal. The most frequently used methods for RNA isolation are based on phenol extraction, precipitation from chaotropic salt solutions, and adsorption on silica (Ausubel et al, 2002), reviewed in my U.S. Pat. Nos. 4,843,155; 5,346,994; and 5,945,515. The method described in the '155 patent is frequently referred to as the single-step method and extracts RNA with a phenol-guanidine solution at pH 4. Its effectiveness and simplicity make the single-step method the most frequently used method for isolating RNA.

An improvement of the single-step method, described in my subsequent '994 patent, allowed simultaneous isolation of RNA, DNA, and proteins from the same sample by phenol-guanidine extraction at pH 4-6. A biological sample is homogenized and the homogenate is subjected to phase separation using a hydrophobic organic solvent such as chloroform or bromochloropropane. Following centrifugation, the mixture separates into the top aqueous phase containing RNA, and the interphase, and organic phase containing DNA and proteins. The aqueous phase is collected and RNA is precipitated and washed with alcohol.

In the single-step method described in the '155 and '994 patents, a careful collection of the separated aqueous phase is critical for the quality of the isolated RNA. Small amounts of the interphase and organic phase can be easily removed together with the aqueous phase, which results in contamination of the isolated RNA with DNA and proteins. Also, collection of the aqueous phase requires a manual approach, which is an obstacle in adapting the single-step method for automation.

The reagents and methods described in the '155 and '994 patents provide substantially pure, undegraded RNA. However, RNA isolated according to the '155 and '994 patents contains a residual amount of genomic DNA, which can be detected by reverse transcription-polymerase chain reaction assay (RT-PCR). Thus, RNA isolated in accord with the '155 and '994 patents must be further purified to render it DNA-free (Guan at al, 2003; Girotti and Zingg, 2003). The contaminating genomic DNA serves as a matrix for DNA polymerase, yielding additional amplification products and distorting RNA-dependent RT-PCR. The DNA contamination in RT-PCR can be only partially alleviated by using a set of primers encompassing exon-intron sequences in the genomic DNA because the presence of pseudogenes, containing no introns, makes this approach unreliable (Mutimer 1998).

Modifications to the single-step method have improved the quality of the isolated RNA. In one modification, RT-PCR inhibitors were removed by adding a lithium chloride precipitation step (Puissant, 1990; Mathy, 1996). In another modification, alcohol precipitation of RNA in the presence of salt increased purity of the isolated RNA (Chomczynski, 1995). These modifications, however, were not effective in removing DNA contamination.

A common practice for removing contaminating DNA is to treat an RNA-containing sample with deoxyribonuclease (DNase). Following DNase treatment, the RNA-containing sample is extracted sequentially with phenol and chloroform. In an effort to limit DNA contamination, an additional DNA precipitation step was included in the single-step method. The contaminating DNA was precipitated from the aqueous phase by adding one-third the volume of 95%$^{w/w}$ ethanol (Siebert, 1993). The final concentration of ethanol was about 24%$^{w/w}$. The author indicated that, at this low ethanol concentration, DNA was precipitated while RNA remained in solution. RNA was precipitated from the solution by adding additional alcohol. This protocol, however, yielded RNA that was still contaminated with DNA, evidenced as a visible band upon analyzing the isolated RNA on an agarose gel stained with ethidium bromide and by RT-PCR.

In another effort to diminish DNA contamination and improve the quality of RNA in the single-step method, Monstein (1995) in a laborious procedure increased the pH of the phenol extraction to pH 4.1-4.7 and treated the sample with proteinase K, followed by another round of phenol extraction, precipitation, and ethanol wash. Despite this prolonged procedure, DNase treatment was still necessary to obtain DNA-free RNA ready for use in RT-PCR.

Separating RNA from DNA was also achieved by phenol extraction at pH 4 without adding guanidine salts (Kedzierski, 1991). However, the absence of guanidine salts during the procedure made RNA susceptible to ribonuclease (RNase), thereby degrading the RNA. A later improvement of this protocol employed phenol extraction buffer at pH 4.2 in the presence of sodium dodecyl sulfate (Chattopadhyay et al., 1993). DNase treatment was also required in the RNA isolation method using a combination of the single-step method followed by the silica column procedure (Bonham, 1996). The use of this double purification protocol decreased DNA contamination, but the isolated RNA still contained genomic DNA that was detected by RT-PCR. Another method for isolating RNA used a monophase aqueous solution containing 10%$^{w/w}$ to 60%$^{w/w}$ phenol (U.S. patent application Publication 20030204077). In the absence of chaotropes, 15%$^{w/w}$ to 55%$^{w/w}$ monoalcohol, diol, or polyol was used to keep phenol in aqueous solution Thus, a residual amount of DNA present in RNA isolated by the methods described in the '155 and '994 patents made it necessary to extend the procedure by including DNase treatment. This diminished the usefulness of the methods by prolonging procedures and unnecessarily exposing RNA to the possibility of degradation during DNase treatment and additional purification steps. However, removing residual DNA from RNA preparations is needed for RT-PCR based microarray determination of gene expression.

Previous methods for isolating RNA, as described in the '155 and '994 patents, were based on phenol extraction performed at pH 4 or higher. None of the previous modifications of the single-step method attempted to improve the quality of RNA by performing phenol extraction at a pH below 4. To the contrary, pH 4 as used in the first '155 patent was increased in the next '994 patent to a pH ranging from 4 to 6. Similarly, the protocol described by Monstein (1995) increased the pH of the phenol extraction to pH 4.7. Another elaborate attempt to improve the single-step method increased the pH of the guanidine-phenol extract to pH 5.2 (Suzuki, 2003).

An alternative to the single-step method of RNA isolation was disclosed in U.S. Pat. No. 5,973,137, using non-chaotropic acidic salts. However, the single-step phenol extraction method is still the most frequently used method for RNA isolation. A publication describing the single-step method (Chomczynski 1987) is the fourth most cited paper in the database of the American Chemical Society and Institute for Scientific Information, and the most cited paper published within the last twenty years (CAS 2003, American Chemical Society).

New methods to enhance purity of isolated RNA are thus desirable.

SUMMARY OF THE INVENTION

The present invention discloses reagents and methods capable of isolating from a biological sample RNA that is substantially free of DNA and thus ready for reverse transcriptase polymerase chain reaction (RT-PCR). Such RNA is termed substantially pure RNA, and is required for proper diagnosis of gene expression in clinical, research and other applications.

One embodiment is a phase separation method using acidic phenol, with RNA separating in the aqueous phase. This is based on the unexpected finding that substantially pure RNA can be isolated by phenol extraction performed at pH below 4.

Another embodiment is acidic phenol precipitation of DNA and protein, with RNA remaining in the soluble fraction. This is based on the unexpected finding that certain concentrations of acidic phenol selectively precipitate DNA, proteins and other cellular components, leaving RNA remaining in a soluble form. The use of acidic phenol for selectively precipitating DNA and proteins eliminates the need for phase separation and also eliminates the use of toxic phase-separation solvents. This approach significantly simplifies the RNA isolation process.

Another embodiment is selective RNA precipitation from solutions containing phenol, a chaotrope, and a low volume of an organic solvent. This embodiment may be used to selectively precipitate RNA molecules up to about 200 nucleotides. Shorter RNA molecules (lower molecular weight RNA) and/or DNA may also be recovered. DNA may also be recovered from the sample by increasing the concentration of organic solvent to at least about $50\%^{w/w}$.

Another embodiment is RNA precipitation from solutions containing at least one salt by adjusting the pH of the solution to a maximum pH of 3.3.

RNA isolated by the inventive compositions and methods can be used directly for RT-PCR because it has a higher purity, that is, there is less contamination of RNA by DNA and/or protein, in comparison to previous methods for RNA isolation such as methods disclosed in U.S. Pat. Nos. 4,843,155; 5,346,994; and 5,945,515, each of which is expressly incorporated herein by reference in its entirety. The RNA that is isolated may be single stranded (ssRNA) or double stranded (dsRNA), and may be isolated from a variety of biological sources, including animals, plants, yeasts, bacteria, and viruses. RNA isolated by the inventive methods and using the inventive compositions may be used in molecular biology, biotechnology, and clinical sciences. In addition, the inventive reagents may be used alone or in combination with other methods for isolating substantially pure DNA (DNA substantially free of RNA and protein), and substantially pure proteins (proteins substantially free of RNA and DNA).

These and other advantages will be apparent in light of the following detailed description and examples.

DETAILED DESCRIPTION

Methods and compositions to prepare purified RNA from biological samples are disclosed. A biological sample is any sample from a biological source, whether in vivo, in vitro, or ex vivo. Samples may be from humans, animals, plants, bacteria, viruses, fungi, parasites, mycoplasmas, etc. Purified RNA is RNA that is substantially undegraded and free of DNA contamination when assayed by reverse transcriptase polymerase chain reaction (RT-PCR).

Phase Separation

One embodiment of the invention provides methods and reagents to enhance the purity of isolated RNA by performing phenol extraction of an RNA-containing sample at a pH below 4.0. In one embodiment, the pH ranges from about pH 3.9 to about pH 3.6. Phenol extraction at a pH below 4.0 more effectively separates RNA from DNA than phenol extraction at pH 4.0 or higher.

The RNA isolating reagent used in the inventive phase separation method comprises an aqueous solution of phenol, and a buffer to maintain the pH within the range from about 3.6 to below pH 4.0. In one embodiment, the pH ranges between pH 3.7 to pH 3.9. The effective concentration of phenol in the RNA isolating reagent ranges from about $10\%^{w/w}$ to about $60\%^{w/w}$. In one embodiment, the concentration of phenol ranges from about $25\%^{w/w}$ to about $45\%^{w/w}$.

The composition may also include other components, such as inhibitors of ribonuclease (RNase), salts, chelating agents, solubilizing agents, detergents, chaotropes, and phenol derivatives.

In some embodiments, RNA in samples having low RNase activity, such as cultured cells, may be extracted with acidic phenol at a pH between about 3.6 to below pH 4.0, and this may sufficiently protect against RNA degradation. However, phenol may not adequately prevent degradation of RNA by cellular RNases derived from the sample or from contaminated labware. Thus, an effective amount of at least one RNase inhibitor may be included in the composition. The RNase inhibitor may be present during sample homogenization and/or during acid phenol extraction. RNase inhibitors include proteinase K, ribonuclease inhibitor from human placenta, vanadyl ribonucleoside complex, and chaotropic salts. Chaotropic salts include guanidine thiocyanate, guanidine hydrochloride, and mixtures of these. In one embodiment, an effective concentration of chaotropic salts ranges from about 0.5 M to about 6 M. In another embodiment, an effective concentration of chaotropic salts ranges from about 2 M to about 4 M.

The buffer may be salts of at least one of acetate, citrate, phosphate, phthalate, tartrate, or lactate. The concentration of buffer should be sufficient to maintain the composition at a pH between about 3.6 to below 4.0. In one embodiment, the pH ranges from about 3.75 to about 3.85. The buffer may be added before or after sample homogenization, either separately or together with the phase separation reagent. Some samples with a high buffering capacity, such as blood and plant tissues, may require an additional amount of acid to adjust the pH within the desired range.

The inventive composition may also contain organic and inorganic salts such as chloride, phosphate, acetate and thiocyanate salts of sodium, potassium, lithium and ammonium. The inventive composition may contain chelating agents such as citrates and ethylenediamine tetraacetate salts. The inventive composition may contain detergents such as polyoxyethylenesorbitan, sodium dodecylsulfate and sarcosine. The salts, chelating agents, and detergents promote tissue solubilization and precipitation of substantially pure RNA. To assist in solubilizing phenol, the aqueous composition may contain a solubilizer or mix of solubilizers. Solubilizers include polyalcohols such as glycerol at a concentration from about $1\%^{w/w}$ to about 10%$^{w/w}$, the upper limit selected so as not to increase DNA contamination of the isolated RNA. Solubilizers also include guanidine salts.

The inventive composition may contain within the about 60%$^{w/w}$ phenol, up to about 5%$^{w/w}$ of phenol derivatives that are less toxic than phenol itself. These derivatives include phenylethanol, propylene phenoxytol, thymol, or butylphenol. In one embodiment these derivatives are present in an amount ranging between about 1%$^{w/w}$ to about 5%$^{w/w}$. The composition may also contain insoluble or partially water-soluble organic compounds, such as cyclohexanol, cyclohexyl bromide, and dichlorobenzoic acid. These compounds increase the density of the composition and substitute for phenol, thereby minimizing the toxicity of the composition.

In one embodiment of the phase separation method, a sample is prepared, typically by homogenization or lysis, in the inventive composition. The bulk of DNA and particulate matter may be removed by sedimentation or filtration from the homogenate or lysate. The homogenate or lysate is separated into aqueous and organic phases by mixing with a hydrophobic organic solvent or mix of solvents, such as chloroform, carbon tetrachloride, bromonaphthalene, bromoanisole or bromochloropropane. The mixture may be sedimented by centrifugation, for example, centrifugation at a temperature in the range between about 4° C. to about 10° C. The top aqueous phase contains RNA, and the interphase and organic phase contains DNA and proteins.

RNA is precipitated from the aqueous phase with a water-soluble organic solvent, such as a lower alcohol. The precipitated RNA is washed by sedimentation or filtration and solubilized in water, formamide, or a buffer. The final RNA preparation is substantially pure, that is, it is undegraded and is essentially free of DNA contamination when tested by RT-PCR.

Additionally, the inventive phase separation method is compatible with the method for the simultaneous isolation of RNA, DNA, and proteins. The DNA and proteins sequestered into the interphase and organic phase may be recovered, as described in Chomczynski, 1993; TRI Reagent brochure, 2003. Alternatively, DNA is precipitated from the organic phase and interphase by adding 0.3 volume of ethanol, followed by precipitation of proteins with a higher amount of ethanol. For example, DNA can be re-extracted from the interphase and organic phase with an aqueous solution at pH 7.0 or higher. Re-extracted DNA is precipitated from the aqueous solution with ethanol. As will be appreciated, the inventive composition and method may be used to isolate substantially pure RNA, substantially pure DNA (that is, DNA essentially free of RNA), and proteins from the same sample. Isolation of all three components allows for correlation of gene expression patterns with changes in the DNA sequence and protein content in biological samples, as well as having numerous other applications.

In one embodiment, the composition used for homogenizing or lysing the sample may lack one or more components, which would be thereafter added to the homogenate or lysate, either alone or together with the phase separation solvent (for example chloroform). In another embodiment, sample homogenization or lysis may be performed above pH 4.0, in which case an acid or a buffer is then added to the homogenized or lysed sample in an amount sufficient to bring the pH of the homogenate or lysate within the range between about 3.6 to below pH 4.0. This amount of acid or buffer may be directly added to the homogenate or lysate, or it may be dissolved in the phase separation solvent. When added together with the phase separation solvent, the acid may be formic acid, acetic acid, trichloroacetic acid, aminocaproic acid, lactic acid, or chlorophenylacetic acid. To promote acid solubility, the phase separation solvent may contain solubilizers such as glycols.

In one embodiment, sample homogenization or lysis is performed in a phenol-free solution containing an RNase inhibitor. After homogenization or lysis, phenol is added to achieve a final concentration ranging from about 10%$^{w/w}$ to about 60%$^{w/w}$ and extraction is performed at pH from about 3.6 to below 4.0. This pH range during extraction is maintained by a buffer that may be part of the aqueous solution, or added to phenol, or may be added separately. After phase separation by centrifugation, RNA is precipitated from the aqueous phase with alcohol. The precipitated RNA is washed and may be dissolved in a solvent such as water, buffer or formamide.

Acidic Phenol Precipitation of DNA Leaving RNA in Supernatant

One embodiment of the invention isolates substantially pure RNA using an acidic phenol solution without performing phase separation. Certain concentrations of acidic phenol selectively precipitate DNA (both single stranded DNA (ss-DNA) and double stranded DNA (dsDNA), proteins, and other cellular components, while RNA remains in a soluble form. This unexpected phenomenon was utilized to elaborate reagents and methods for isolating RNA without separating aqueous and organic phases and the interphase.

The acidic phenol precipitation method simplifies the process of RNA isolation. It also eliminates toxic organic solvents that may be used in the phase separation method. The composition propels DNA and proteins to form a firm pellet at the bottom of a tube, which alleviates the danger of accidental transfer of DNA and protein molecules to the supernatant fraction containing RNA. The supernatant can be securely collected by pipetting, siphoning, decanting, or filtering, each of which may be automated for use in an automated procedure for RNA isolation. Additionally, the entire acidic phenol precipitation method may occur at room temperature, which eliminates the need for a refrigerated centrifuge that may be used in the phase separation method.

The composition used for acidic phenol precipitation comprises an aqueous solution of phenol at a concentration ranging from about 3%$^{w/w}$ to less than 30%$^{w/w}$. In one embodiment, the phenol concentration ranges from about 3%$^{w/w}$ to about 25%$^{w/w}$. In another embodiment, the phenol concentration is in the range between about 8%$^{w/w}$ to about 20%$^{w/w}$. The phenol concentrations in the acid precipitation embodiment are lower than the 30%$^{w/w}$ phenol to 60%$^{w/w}$ phenol concentrations described in the '155 and '994 patents.

The inventive composition is acidified with a buffer or an acid in an amount sufficient to maintain the pH within a range from about 3.6 to about 5.5. In one embodiment, the pH ranges from about 3.9 to about 4.5. The buffer can be selected from organic or inorganic buffers including, but not limited to, acetate, citrate, phosphate, phthalate, tartrate, and/or lactate.

To enhance the efficiency of RNA isolation, acidic phenol may be supplemented with RNase inhibitors, salts, chelating agents, phenol solubilizing agents and/or detergents. RNase inhibitors include vanadyl ribonucleoside complex and proteinase K or combinations of these inhibitors. RNase inhibitors also include chaotropic agents or chaotropes such as guanidine salts at concentrations ranging from about 0.5 M to about 6 M. In one embodiment, the concentration of the chaotropes is from about 1.5 M to about 2.5 M. Chaotropic salts may serve as phenol solubilizers by maintaining phenol in aqueous solution. The acidic phenol composition may further contain organic and/or inorganic salts such as chloride, phosphate, acetate, citrate and thiocyanate salts of sodium, potassium, lithium, and ammonium. The composition may also contain chelating agents such as citrates and ethylenediamine tetraacetate salts. The composition may also contain detergents including polyoxyethylenesorbitan, sodium dodecylsulfate, and sarcosine. The composition may also contain up to $5\%^{w/w}$ of solvents and reagents that are less toxic than phenol, such as thymol, phenylethanol, cyclohexanol, cyclohexyl bromide and dichlorobenzoic acid. These additional components promote tissue solubilization and precipitation of pure RNA.

The acidic phenol precipitation reagent may contain an additional solubilizer or mix of solubilizers to help maintain phenol in aqueous solution. Phenol solubilizing agents include glycols, polyalcohols, and lower alcohols. These can be added to the acidic phenol precipitation reagent in amounts from about $1\%^{w/w}$ to about $10\%^{w/w}$, the upper limit selected so as not to increase DNA contamination of the isolated RNA.

In one embodiment of the acidic phenol precipitation method, a biological sample is homogenized or lysed in the precipitation reagent. The resulted homogenate or lysate is centrifuged or filtered to remove precipitated DNA, proteins, and other cellular components. RNA remains in a soluble form and is subsequently precipitated from the supernatant with a water-soluble organic solvent, such as lower alcohols including methanol, ethanol, propanol, isopropanol, and butanol. The RNA pellet is then washed and may be dissolved in water, buffer, or formamide.

In the another embodiment of the acidic phenol precipitation method, a biological sample is homogenized in about 3 times (3x) to about 1.5 times (1.5x) concentrated acidic phenol precipitation reagent. The use of a concentrated reagent allows processing of solid tissues as well as high volume liquid samples using one reagent. A high volume of a liquid sample can be compensated by adding to the concentrated reagent a smaller amount of water. The concentrated reagent dissolves most of the components in a biological sample and effectively releases RNA from cellular structures. For example, a sample may be homogenized in two times (2x) concentrated reagent. Following homogenization, an equal volume of water is mixed with the homogenate. The addition of water brings phenol, guanidine, and other ingredients within the desired concentration. This creates conditions for effectively precipitating and removing DNA and proteins from an RNA containing sample.

After centrifugation or filtration of the homogenate or lysate, RNA remains in the supernatant or filtrate, while DNA, protein, and other cellular components form a firm pellet at the bottom of a tube. RNA is precipitated from the supernatant or filtrate with a water-soluble organic solvent as previously described. The RNA precipitate is washed and may be dissolved in water, buffer, or formamide.

In one embodiment of the invention, a single reagent may be used in either the phase separation method or the acidic phenol precipitation method. This dual use reagent comprises components of the reagent used in the phase separation method and a 2x concentration of reagent used in the acidic phenol precipitation method. As previously described, the pH for the phase separation method may be between about pH 3.6 to below pH 4.0, and the pH for the acidic phenol precipitation method may be between about pH 3.6 to about pH 5.5. In the dual use embodiment, a pH adjustment of the reagent is therefore necessary before switching from one method to the other method. For example, the 2x reagent for the acidic phenol precipitation method at pH 4.2 must be further acidified to a pH below 4.0 before use in the phase separation method.

The inventive phase separation method may be used for specimens containing high amounts of fats, such as fat tissue and certain tumor or neoplastic tissues. Samples with a high level of contaminants, such as plants and fat-containing tissues, may be processed by the dual use procedure, which combines the acidic phenol precipitation method and the phase separation method. In one embodiment, a biological sample is homogenized in 2x acidic phenol precipitation reagent. The homogenate is then diluted with water to approach the concentration range of the acidic phenol precipitation reagent (that is, about $3\%^{w/w}$ phenol to less than $30\%^{w/w}$ phenol). After dilution, precipitated DNA, proteins and other cellular components are removed by sedimentation or filtration. The resulting supernatant or filtrate is collected and mixed with a phase separation solvent. In one embodiment, 0.05 volume to 0.01 volume of a phase separation solvent is added per one volume of the supernatant. The phase separation solvent or mix of solvents is at least one hydrophobic solvent including, but not limited to, caprolactone, ethylene glycol diacetate, polyethylene glycol dibenzoate, as well as solvents used for the phase separation method. The mixture is centrifuged to obtain a top aqueous phase, an interphase, and an organic phase. The aqueous phase containing RNA is collected and mixed with one volume of a lower alcohol to precipitate RNA. The precipitated RNA is washed and dissolved in water, buffer, or formamide.

The methods providing purified RNA based on the inventive acidic phenol solutions are useful for gene expression profiling with RT-PCR based microarrays used in biotechnology, molecular biology and clinical applications. This can be exemplified by the detection of specific gene expression patterns in cancer cells and other type of pathological specimens.

Selective RNA Precipitation Using Low Volume Organic Solvent

As previously described, RNA may be precipitated from the aqueous phase in the inventive phase separation method, and from the inventive acidic phenol composition. In each case, RNA is precipitated by adding about one volume of an organic solvent to approach a final organic solvent concentration of about $50\%^{w/w}$. However, in some sample preparations, one volume of organic solvent co-precipitates polysaccharides and proteins, such as proteoglycans, together with RNA. Previously, to avoid co-precipitation of contaminants, one method modified the single-step RNA purification method by employing $25\%^{w/w}$ alcohol in the presence of 0.9 M sodium ions to precipitate RNA (Chomczynski, 1995). Another method treated a phenol-free chaotrope solution with $13\%^{w/w}$ to $23\%^{w/w}$ of an organic solvent, with the pH of the solution remaining within the range of pH 6 to pH 7.5 to precipitate RNA.

In the present inventive method, substantially pure RNA is precipitated from phenol-chaotrope solutions by adding an organic solvent or mix of solvents to achieve a final concentration of about $10\%^{w/w}$ to about $40\%^{w/w}$ organic solvent. The organic solvent(s) may be acetone, tetramethylene sulfone, lower alcohols, glycols, polyalcohols, acetone, ethyleneglycol diacetate, and/or methyl sulfoxide. This method provides substantially pure RNA when precipitating RNA from either the aqueous phase in the phase separation method, or in the acidic phenol precipitation method from the DNA- and protein-free supernatant. The method does not require adding salts to a phenol-chaotrope solution.

It was unexpected that substantially pure RNA precipitated from a phenol-chaotrope solution at about 10%$^{w/w}$ to about 40%$^{w/w}$ concentration of an organic solvent without supplementing the solution with salt, as was earlier suggested (Chomczynski 1995). In fact, adding salt along with alcohol decreased the purity of the isolated RNA. The finding that 10%$^{w/w}$ to 40%$^{w/w}$ alcohol alone precipitated RNA from the phenol-chaotrope solution was also contrary to a report where DNA precipitated and RNA remained in a soluble form by adding 0.3 volume of alcohol (final concentration 24%$^{w/w}$) to the phenol-chaotrope solution (Siebert, 1993).

In one embodiment, the final concentration of organic solvent(s) in the composition is from about 20%$^{w/w}$ to about 25%$^{w/w}$. In another embodiment, the final concentration of organic solvent(s) in the composition is from about 10% to about 40%. The pH of the phenol-chaotrope solution may range from about pH 2.0 to about pH 9.0. In one embodiment, the pH of the phenol-chaotrope solution ranges from about pH 3.5 to about pH 5.0.

Organic solvents at concentrations from about 10%$^{w/w}$ to about 40%$^{w/w}$ precipitate RNA molecules greater than about 200 bases, considered as higher molecular weight RNA. RNA fragments less than about 200 bases, along with polysaccharides and proteoglycans, remain in solution. Following precipitation of higher molecular weight RNA, the smaller molecular weight RNA can be recovered from the solution by precipitating with an additional amount of organic solvent to approach a final concentration of about 50%$^{w/w}$ or higher, for example, to about 90%$^{w/w}$.

The inventive method, whereby RNA is precipitated using about 10%$^{w/w}$ to about 40%$^{w/w}$ of an organic solvent, can also be used to decrease the amount of contaminating DNA in RNA preparations. This selective precipitation of RNA is effective only when a small amount of contaminating DNA is present in the solutions, for example, less than 10 ng DNA per 1 μg RNA. Precipitating RNA using about 10%$^{w/w}$ to about 40%$^{w/w}$ of an organic solvent also improves the quality of RNA isolated, such that a high yield of substantially pure and undegraded RNA is obtained, in accord with the method described in my previous '155 and '994 patents.

Acidic RNA Precipitation from Salt-Containing Solutions

Substantially pure RNA, along with DNA, may be obtained from aqueous solutions containing salts by pH-dependent precipitation of RNA at a pH below about 3.3. Precipitating RNA from salt solutions at an acidic pH is contrary to that reported in U.S. Pat. No. 5,973,137. The '137 patent discloses that, in solutions at pH below 6, non-chaotropic salts precipitate DNA, while RNA stays in a soluble form.

In the inventive method, a buffer acid is added to the RNA solution in an amount sufficient to result in a pH of 3.3 or lower. In one embodiment, the resulting pH is in the range from about pH 3.0 to about pH 2.7. The acid may be an organic acid or an inorganic acid. The acid may be hydrochloric acid, phosphoric acid, acetic acid, and/or lactic acid. In one embodiment, salts in the composition may be guanidine salts.

This embodiment may be incorporated into either the inventive phase separation method and/or the inventive acidic phenol precipitation method. For use in the acidic phenol precipitation method, acids or buffers can be dissolved either in water or in organic solvents. The acid selectively precipitates RNA, leaving polysaccharides and protein in a soluble form. The volume of acid used to precipitate RNA is small, permitting a low sample volume during RNA isolation. In one embodiment, the volume of acid ranges from about 0.1%$^{w/w}$ to about 25%$^{w/w}$ of the volume of RNA solution.

The precipitation of RNA with a low amount of an organic solvent and with acidic pH, described in the present invention, can also be used to improve the quality of RNA using methods disclosed in my previous '155 and '994 patents.

Treating an RNA-containing sample obtained by RNA precipitation with a low volume of an organic solvent or acidic precipitation of RNA from salt-containing solutions precipitates higher molecular weight RNA. Higher molecular weight RNA includes ribosomal RNA (rRNA, for example 18S and 28S RNA) and messenger RNA (mRNA). The remaining lower molecular weight RNA is less than about 200 nucleotides, and includes transfer RNA (tRNA), 5S RNA, and small interfering RNA (siRNA) that regulates gene expression. Lower molecular weight RNA is recovered from the above-described solution by treatment with an additional volume of an organic solvent. In one embodiment, the sample is treated with one volume of a lower alcohol, for example, methanol, ethanol, propanol, etc. to precipitate low molecular weight RNA.

Exemplary solutions and methods of the present invention are described in the following working Examples.

Example 1

Phase Separation Isolation of RNA from Rat Liver

In one embodiment, the following composition was used for phase separation of RNA: 4 M guanidine thiocyanate, 0.2 M ammonium thiocyanate, 5%$^{w/w}$ glycerol, 40%$^{w/w}$ phenol, 0.1%$^{w/w}$ sarcosine, 10 mM sodium citrate, and 0.1 M sodium acetate buffer, pH 3.8.

Rat liver (38 mg) was homogenized in 1.5 ml of the above composition. Thereafter, 0.15 ml of bromochloropropane was added to the homogenate. The resulting mixture was shaken and sedimented for fifteen minutes at 4° C. at 12,000× g. Following sedimentation, an aqueous phase, an interphase, and a lower organic phase formed. RNA sequestered into the aqueous phase, while DNA and proteins sequestered into the interphase and organic phase.

RNA was precipitated from the aqueous phase by adding 0.75 ml of isopropanol. The RNA precipitate was centrifuged for five minutes at 10,000×g. The resulting pellet was washed with 0.75 ml of 75%$^{w/w}$ ethanol and centrifuged for five minutes at 10,000×g. The final RNA pellet was dissolved in water and the RNA concentration was determined spectrophotometrically at $A_{260/280}$ by methods known to one skilled in the art.

The yield of RNA was 0.22 mg. The $A_{260/280}$ ratio was 1.76, which indicated the lack of protein contamination. The isolated RNA was successfully utilized for RT-PCR using primers for glyceraldehydes 3-phosphate dehydrogenase (GAPDH), actin, and c-fos genes. Reverse transcription was performed using SuperScript transcriptase from Invitrogen (Carlsbad Calif.) and PCR was performed using Taq DNA polymerase from Sigma (St. Louis Mo.). RT-PCR products were analyzed on a 1% agarose-ethidium bromide gel. No DNA was detected in the isolated RNA in the absence of reverse transcription. Northern blot analysis of the isolated RNA was performed using 1%-formaldehyde-agarose gels and transferred to a nylon membrane. Ethidium bromide and methylene blue staining showed undegraded ribosomal bands. Hybridization with biotin-labeled probes showed undegraded bands of mRNA for GAPDH, actin, and c-fos.

Example 2

Phase Separation Isolation of RNA from Human Blood

Human blood (0.5 ml) was mixed with 75 μl of glacial acetic acid and 5 ml of the composition described in Example 1. Thereafter, 0.5 ml of bromochloropropane was added to the mixture. The mixture was shaken and sedimented for fifteen minutes at 4° C. at 12,000×g. Following sedimentation, the mixture formed an aqueous phase, an interphase, and a lower organic phase. RNA sequestered into the aqueous phase, while DNA and proteins sequestered into the interphase and organic phase.

RNA was precipitated from the aqueous phase by adding 1.25 ml of isopropanol. The RNA precipitate was centrifuged for five minutes at 12,000×g. The resulting pellet was washed with five ml of 75% ethanol and centrifuged for five minutes at 10,000×g. The final RNA pellet was dissolved in water and the RNA concentration was determined spectrophotometrically at $A_{260/280}$ by methods known to one skilled in the art.

The yield of RNA was 18.9 μg. The $A_{260/280}$ ratio was 1.70, which indicated the lack of protein contamination. The isolated RNA was successfully utilized for RT-PCR using GAPDH primers. No DNA contamination was detected by PCR of the isolated RNA without reverse transcription. Northern blot analysis of the isolated RNA showed undegraded bands of ribosomal RNA and an undegraded band of GAPDH mRNA.

Example 3

Isolation of RNA by Phase Separation and Acidified Bromochloropropane

Rat spleen (21 mg) was homogenized in 1 ml of an aqueous solution containing 3.5 M guanidine thiocyanate, 50 mM potassium acetate, 43%$^{w/w}$ phenol, 0.1% Triton X-100, pH 4.1. The homogenate was centrifuged at 12,000×g for ten minutes to remove the bulk of DNA and particulates. The clear homogenate was mixed with 0.1 ml of bromochloropropane containing 14%$^{w/w}$ acetic acid. The resulting pH of the mixture was pH 3.7. The mixture was shaken and sedimented for ten minutes at 4° C. at 12,000×g. Following sedimentation, the mixture formed an aqueous phase, an interphase, and a lower organic phase. RNA sequestered into the aqueous phase, while DNA and proteins sequestered into the interphase and organic phase.

RNA was selectively precipitated from the aqueous phase by adding 0.5 ml ethanol. The precipitated RNA was sedimented for five minutes at 10,000×g, then washed with 75%$^{w/w}$ ethanol and sedimented for five minutes at 10,000×g. The final RNA pellet was dissolved in water and the RNA concentration was determined spectrophotometrically at $A_{260/280}$ by methods known to one skilled in the art.

The yield of RNA was 77 μl. The $A_{260/280}$ ratio was 1.74, which indicated the lack of protein contamination. The isolated RNA was successfully utilized for RT-PCR using GAPDH primers and no DNA contamination was detected. Northern blot analysis of the isolated RNA showed undegraded bands of ribosomal RNA and an undegraded band of GAPDH mRNA.

Example 4

Isolation of RNA by Phase Separation and Homogenization in a Phenol-Free Chaotrope Solution Rat skeletal muscle (29 mg) was homogenized in 0.5 ml of an aqueous solution of 3 M guanidine thiocyanate and 5 mM sodium acetate. The homogenate was mixed with 0.5 ml of phenol and 0.1 M sodium acetate buffer, pH 3.7. The resulting mixture was shaken with 0.1 ml of bromochloropropane and sedimented for fifteen minutes at 4° C. at 12,000×g. Following sedimentation, the mixture formed an aqueous phase, an interphase, and a lower organic phase. RNA sequestered into the aqueous phase, while DNA and proteins sequestered into the interphase and organic phase.

RNA was selectively precipitated from the aqueous phase by adding 0.5 ml of an aqueous solution containing 50%$^{w/w}$ ethanol. The RNA precipitate was washed, treated, and assayed as described in Example 1.

The yield of RNA was 16 μg. The $A_{260/280}$ ratio was 1.70, which indicated the lack of protein contamination. The isolated RNA was successfully utilized for RT-PCR using GAPDH primers and no DNA contamination was detected. Northern blot analysis of the isolated RNA showed undegraded bands of ribosomal RNA and an undegraded band of GAPDH mRNA.

Example 5

Isolation of RNA by Phase Separation with Homogenization in 1%$^{w/w}$ Sodium Dodecyl Sulfate A primary culture of human fibroblast cells (Clonetics, San Diego Calif.) grown in a 25 cm$^2$ plastic bottle was overlaid with 1.5 ml of a solution containing 1%$^{w/w}$ sodium dodecyl sulfate and 10 mM sodium citrate, pH 7.0, supplemented with 50 μg/ml proteinase K. The resulting cell solution was incubated for one hour at room temperature (about 20° C.), transferred to a centrifuge tube, and mixed with 1.5 ml of acidic phenol containing 12%$^{w/w}$ water and 100 mM sodium acetate, pH 3.7. After centrifugation for fifteen minutes at 4° C., the mixture formed an aqueous phase, an interphase, and an organic phase. Following phase separation, RNA sequestered into the aqueous phase, while DNA and proteins sequestered into the interphase and organic phase, respectively.

RNA was precipitated from the aqueous phase by adding 0.75 ml of ethanol and sedimenting for five minutes at 10,000×g. The RNA pellet was washed with 75% ethanol, centrifuged for five minutes at 10,000×g, and dissolved in water.

The yield of RNA was 18 μg. The $A_{260/280}$ ratio was 1.71, which indicated the lack of protein contamination. The isolated RNA was successfully utilized for RT-PCR using GAPDH primers and no DNA contamination was detected.

Northern blot analysis of the isolated RNA showed undegraded bands of ribosomal RNA and an undegraded band of GAPDH mRNA.

Example 6

Isolation of RNA by Acidic Phenol Precipitation

In one embodiment, the following composition was used for acidic phenol precipitation of RNA: 20%$^{w/w}$ phenol, 2 M guanidine thiocyanate, 15 mM sodium citrate, 0.1 M lithium chloride, 0.05%$^{w/w}$ sarcosine, 1.5%$^{w/w}$ glycerol, and sodium acetate buffer, pH 4.2. Rat liver (52 mg) was homogenized in 1 ml of this composition. The homogenate was centrifuged at 10,000×g for five minutes at room temperature (about 20° C.) to remove precipitated DNA, protein, and cellular components.

The resulting supernatant was transferred to a clean tube and was mixed with 1 ml of ethanol to precipitate RNA. Precipitated RNA was sedimented at 10,000×g for five minutes, washed with 75%$^{w/w}$ ethanol, and dissolved in water.

The yield of RNA was 187 μg. The $A_{260/280}$ ratio was 1.74, which indicated the lack of protein contamination. The isolated RNA was successfully utilized for RT-PCR using GAPDH primers and no DNA contamination was detected. Northern blot analysis of the isolated RNA showed undegraded bands of ribosomal RNA and an undegraded band of GAPDH mRNA.

Example 7

Isolation of RNA by Acidic Phenol Precipitation Using Two Times Concentrated Reagent Rat liver (47 mg) was homogenized in 1 ml of the reagent described in Example 6 at two times the concentration indicated in Example 6. The concentrated reagent contained additionally 1%$^{w/w}$ phenylethanol. The homogenate was mixed with 1 ml water to form the precipitating reagent.

The precipitated DNA, proteins and other cellular components were sedimented by centrifugation at 10,000×g for five minutes at room temperature (about 20° C.). The resulting supernatant was transferred to a clean tube and mixed with 1 ml ethanol to precipitate RNA. Precipitated RNA was sedimented at 10,000×g for 5 minutes, washed with 75%$^{w/w}$ ethanol, and dissolved in water.

The yield of RNA was 178 μg. The $A_{260/280}$ ratio was 1.77, which indicated the lack of protein contamination. The isolated RNA was successfully utilized for RT-PCR using GAPDH primers and no DNA contamination was detected. Northern blot analysis of the isolated RNA showed undegraded bands of ribosomal RNA and an undegraded band of GAPDH mRNA.

Example 8

Isolation of RNA by the Inventive Two-Step Procedure

Rat brain (61 mg) was homogenized in 1 ml of the two times concentrated reagent described in Example 7. The homogenate was mixed with 1 ml water and the resulting mixture was centrifuged at 10,000×g for five minutes at room temperature (about 20° C.) to remove precipitated DNA, protein, and cellular components. The supernatant was transferred to a clean tube and mixed with 0.05 ml of bromochloropropane. The mixture was centrifuged and separated into a top aqueous phase, an interphase, and an organic phase.

The aqueous phase containing RNA was transferred to a fresh tube and was acidified to pH 2.9 with 5 M lactic acid in isopropanol. The RNA precipitate was sedimented at 10,000×g for five minutes, washed with 75%$^{w/w}$ ethanol, and dissolved in water.

The yield of RNA was 33 μg. The $A_{260/280}$ ratio was 1.77, which indicated the lack of protein contamination. The isolated RNA was successfully utilized for RT-PCR using GAPDH primers and no DNA contamination was detected. Northern blot analysis of the isolated RNA showed undegraded bands of ribosomal RNA and an undegraded band of GAPDH mRNA.

Other variations or embodiments of the invention will also be apparent to one of ordinary skill in the art from the above description and examples. Thus, the forgoing embodiments are not to be construed as limiting the scope of this invention.

What is claimed is:

1. A method for isolating purified RNA from a biological sample comprising
    a) treating the biological sample with a reagent comprising phenol that when added to the biological sample at a final phenol concentration is from about 10%$^{w/w}$ to about 60%$^{w/w}$ and at least one ribonuclease inhibitor,
    b) mixing the mixture containing biological sample from step (a) with at least one hydrophobic solvent and a buffer at a concentration sufficient to maintain a pH in the range from about pH 3.6 to below pH 4.0,
    c) separating an aqueous phase from the mixture obtained in step (b) by sedimentation and recovering purified RNA from an aqueous phase by precipitation with about an equal volume of a water-soluble organic solvent which is RNA that does not reveal the presence of DNA when assayed by reverse transcription polymerase chain reaction (RT-PCR), and
    d) washing and solubilizing the precipitated RNA.

2. The method of claim 1 wherein the reagent in (a) further comprises a buffer selected from at least one of acetate, citrate, phosphate, phthalate, tartrate, lactate, or mixtures thereof.

3. The method of claim 1 wherewith the ribonuclease inhibitor is selected from at least one of proteinase K, ribonuclease inhibitor from human placenta, vanadyl ribonucleoside complex, chaotropic salts, or mixtures thereof.

4. The method of claim 3 wherein the chaotropic salts are selected from at least one of urea salts, guanidine salts, or mixtures thereof.

5. The method of claim 4 wherein the guanidine salts are selected from at least one of guanidine thiocyanate or guanidine hydrochloride at a final concentration in the range of about 0.5 M to about 6 M.

6. The method of claim 1 wherein the reagent in (a) further comprises a detergent at a concentration <0.1%$^{w/w}$.

7. The method of claim 6 wherein the detergent is selected from at least one of sarcosine, polyoxyethylenesorbitan, a dodecylsulfate salt, or mixtures thereof.

8. The method of claim 1 wherein the reagent in (a) further comprises an inorganic or organic salt and a chelating agent.

9. The method of claim 8 wherein the inorganic or organic salt is selected from at least one of chlorides, phosphates, bromates, acetates, citrates, phthalates, tartrates, lactates, or thiocyanates of sodium, potassium, lithium or ammonium.

10. The method of claim 8 wherein the chelating agent is selected from at least one of citrates, ethylenediamine tetraacetic salts, or mixtures thereof.

11. The method of claim 1 wherein the reagent in (a) further comprises phenol solubilizers selected from at least one of polyalcohols, monoalcohols, and guanidine salts.

12. A method for isolating purified RNA from a biological sample comprising
   a) treating the sample with a phenol-free composition comprising
      at least one hydrophobic organic solvent at a final concentration in the range from about $10\%^{w/w}$ to about $40\%^{w/w}$, and at least one acid sufficient to maintain a pH in the range of about pH 3.6 to below pH 4.0 during phase separation, and an optional acid solubilizer, or
      at least one ribonuclease inhibitor and a buffer selected from at least one of acetate, citrate, phosphate, phthalate, tartrate, lactate, or mixtures thereof, sufficient to maintain a pH of the composition in the range from about pH 3.6 to below pH 4.0;
   b) then treating the sample with a reagent comprising phenol at a final concentration ranging from about $10\%^{w/w}$ to about $60\%^{w/w}$ and at least one ribonuclease inhibitor;
   c) mixing the sample with at least one hydrophobic solvent while maintaining a pH in the range from about pH 3.6 to below pH 4.0;
   d) recovering purified RNA from an aqueous phase to which about an equal volume of a water-soluble organic solvent is added to precipitate the purified RNA which is RNA that does not reveal the presence of DNA when assayed by reverse transcription polymerase chain reaction (RT-PCR); and
   e) washing and solubilizing the precipitated RNA.

13. The method according to claim 1 or 12 wherein step (a) is performed at a pH ranging from about pH 3.9 to about pH 9.0, and the sample is then adjusted to a pH ranging from about pH 3.6 to below pH 4.0.

14. An acidic phenol precipitation method for isolating purified RNA from a biological sample comprising the steps of
   a) treating the biological sample with a mono-phase reagent comprising phenol at a final concentration ranging from about $3\%^{w/w}$ to less than $30\%^{w/w}$ and a buffer sufficient to maintain a pH of the resulting mixture containing biological sample in the range from about pH 3.6 to about pH 5.5,
   b) sedimenting or filtering the mixture containing biological sample to obtain a purified biological sample substantially free of DNA, proteins, and cellular components without the use of a hydrophobic solvent and performing phase separation and wherein the pH of the mixture containing biological sample remains in the range from about pH 3.6 to about pH 5.5,
   c) adding to the purified biological sample about an equal volume of a water-soluble organic solvent to precipitate purified RNA which is RNA that does not reveal the presence of DNA when assayed by reverse transcription polymerase chain reaction (RT-PCR),
   d) sedimenting or filtering the precipitated RNA, and
   e) washing and solubilizing the precipitated RNA.

15. A two-step method for isolating purified RNA from a biological sample comprising
   a) treating the biological sample with a mono-phase reagent comprising phenol at a final concentration ranging from about $3\%^{w/w}$ to less than $30\%^{w/w}$, at least one chaotrope, and a buffer sufficient to maintain a pH of the resulting mixture containing biological sample in the range from about pH 3.6 to about pH 5.5,
   b) sedimenting or filtering the mixture containing biological sample to obtain a purified biological sample substantially free of DNA, proteins, and cellular components,
   c) adding to the purified biological sample at least one hydrophobic organic solvent and a buffer in a concentration sufficient to maintain a pH of the purified biological sample in the range from about pH 3.6 to below pH 4.0,
   d) recovering purified RNA from an aqueous phase to which about an equal volume of a water soluble organic solvent is added to precipitate purified RNA which is RNA that does not reveal the presence of DNA when assayed by reverse transcription polymerase chain reaction (RT-PCR),
   e) sedimenting or filtrating the precipitated RNA, and
   f) washing and solubilizing the precipitated RNA.

16. The method of claim 15 where the hydrophobic organic solvent is sufficiently dense to separate the organic phase during phase separation.

17. The method according to claim 15 wherein the hydrophobic organic solvent is selected from at least one of caprolactone, ethylene glycol diacetate, polyethylene glycol dibenzoate, chloroform, carbon tetrachloride, bromochloropropane, bromonaphthalene, bromoanisole, or mixtures thereof.

18. The method according to claim 14 or 15 wherein the sample is treated with the composition of (a) at about 1.5× to about 2.5× concentration, and the resulting sample is diluted to approach the non-concentrated solution.

19. The method according to any of claims 1, 12, 14, or 15 wherein the solvent added to precipitate RNA is at least one of lower alcohols, polyalcohols, acetone, ethyleneglycol diacetate, methyl sulfoxide, or mixtures thereof.

20. A method for selectively precipitating higher molecular weight RNA from a biological sample comprising
   treating the biological sample with an aqueous composition comprising phenol at a final concentration ranging from about $1\%^{w/w}$ to about $60\%^{w/w}$, at least one chaotrope, a buffer in a concentration sufficient to maintain a pH of the composition in the range from about pH 2.0 to about pH 9.0, at least one water-soluble organic solvent at a concentration from about $10\%^{w/w}$ to about $40\%^{w/w}$ to selectively precipitate RNA molecules greater than 200 based from the biological sample, and
   precipitating purified higher molecular weight RNA from the biological sample.

21. The method of claim 20 further comprising the step of thereafter adding additional organic solvent sufficient to increase the concentration of organic solvent to at least $50\%^{w/w}$ to precipitate lower molecular weight RNA, and precipitating purified lower molecular weight RNA from the sample.

22. The method of claim 20 comprising preparing the biological sample according to any of claims 1, 12, 14, or 15 to obtain an aqueous solution of RNA, and precipitating RNA from the aqueous solution.

23. A method for isolating purified RNA from a biological sample comprising
   a) treating the sample with a reagent comprising phenol at a final concentration ranging from about $10\%^{w/w}$ to about $60\%^{w/w}$ and at least one ribonuclease inhibitor, the phenol comprising derivative selected from at least one of phenylethanol, propylene phenoxytol, thymol, butylphenol, or mixtures thereof at a final concentration up to about $5\%^{w/w}$, b) mixing the sample with at least one hydrophobic solvent while maintaining a pH in the range from about pH 3.6 to below pH 4.0, c) recovering purified RNA from an aqueous phase to which about an equal volume of a water-soluble organic solvent is added to precipitate the purified RNA, and d) washing and solubilizing the precipitated RNA.

24. A method for isolating purified RNA from a biological sample comprising a) treating the sample with a reagent comprising phenol at a final concentration ranging from about $10\%^{w/w}$ to about $60\%^{w/w}$, at least one ribonuclease inhibitor, and an organic compound selected from at least one of cyclohexyl bromide, dibromopropane, dichlorobenzoic acid, and mixtures thereof in a concentration ranging from about $1\%^{w/w}$ to about $5\%^{w/w}$ sufficient to increase the density of the composition, b) mixing the sample with at least one hydrophobic solvent while maintaining a pH in the range from about pH 3.6 to below pH 4.0, c) recovering purified RNA from an aqueous phase to which about an equal volume of a water-soluble organic solvent is added to precipitate the purified RNA, and d) washing and solubilizing the precipitated RNA.

\* \* \* \* \*